(12) United States Patent
Sappok et al.

(10) Patent No.: US 10,309,953 B2
(45) Date of Patent: Jun. 4, 2019

(54) FILTER RETENTATE ANALYSIS AND DIAGNOSTICS

(71) Applicant: Filter Sensing Technologies, Inc., Malden, MA (US)

(72) Inventors: Alexander Sappok, Cambridge, MA (US); Leslie Bromberg, Sharon, MA (US); Paul Ragaller, Dorchester, MA (US)

(73) Assignee: CTS CORPORATION, Lisle, IL (US)

( * ) Notice: Subject to any disclaimer, the term of this patent is extended or adjusted under 35 U.S.C. 154(b) by 0 days.

(21) Appl. No.: 14/887,771

(22) Filed: Oct. 20, 2015

(65) Prior Publication Data
US 2016/0109425 A1     Apr. 21, 2016

Related U.S. Application Data

(60) Provisional application No. 62/065,761, filed on Oct. 20, 2014.

(51) Int. Cl.
*F01N 3/021* (2006.01)
*F01N 3/023* (2006.01)
(Continued)

(52) U.S. Cl.
CPC ..... *G01N 33/2835* (2013.01); *B01D 46/0086* (2013.01); *F01N 3/021* (2013.01);
(Continued)

(58) Field of Classification Search
CPC ............ G01N 33/2835; G01N 1/2252; B01D 46/0086; F01N 3/0232; F01N 3/0233; F01N 3/021
(Continued)

(56) References Cited

U.S. PATENT DOCUMENTS 4,024,452 A    5/1977   Seidel
4,042,879 A    8/1977   Ho et al.
(Continued)

FOREIGN PATENT DOCUMENTS

CN          1032238 A     4/1989
CN      101078692 A    11/2007
(Continued)

OTHER PUBLICATIONS

Rights et al: "Tille Preparation and characterisation of ceria particles," 2013; Retrieved from the Internet: URL:htts:// ::ora.ucc.ie/bitstream/handle/10468/1141 /MorrisVNA_ PhD2013 .pdf.

*Primary Examiner* — Lisa M Caputo
*Assistant Examiner* — Suman K Nath
(74) *Attorney, Agent, or Firm* — Daniel Deneufbourg

(57) ABSTRACT

A filter retentate analysis system and method is disclosed, which provides information to diagnose the current and historical state of a system generating the retentate or through which the retentate has passed. The disclosure describes the analysis of retentate characteristics which may include the composition, amount, distribution, and physical or chemical properties of the retentate useful to monitor or diagnose the state, health, or operating history of a system or sub-system. The analysis is broadly applicable to wide range of systems and process ranging from engines and exhaust systems to production plants and equipment.

9 Claims, 1 Drawing Sheet

(51) Int. Cl.
  *G01N 33/28* (2006.01)
  *B01D 46/00* (2006.01)
  *G01N 1/22* (2006.01)

(52) U.S. Cl.
  CPC .......... *F01N 3/0232* (2013.01); *F01N 3/0233* (2013.01); *G01N 1/2252* (2013.01)

(58) Field of Classification Search
  USPC ................................. 73/61.63, 61.41, 61.42
  See application file for complete search history.

(56) References Cited

U.S. PATENT DOCUMENTS

| | | |
|---|---|---|
| 4,477,771 A | 10/1984 | Nagy et al. |
| 4,689,553 A | 8/1987 | Haddox |
| 5,074,112 A | 12/1991 | Walton |
| 5,103,181 A | 4/1992 | Gaisford et al. |
| 5,142,595 A | 8/1992 | Chester |
| 5,157,340 A | 10/1992 | Walton et al. |
| 5,369,369 A | 11/1994 | Cutmore |
| 5,423,180 A | 6/1995 | Nobue et al. |
| 5,447,635 A | 9/1995 | Viscardi et al. |
| 5,497,099 A * | 3/1996 | Walton ................. B01D 46/46 324/639 |
| 5,500,599 A | 3/1996 | Stange |
| 5,557,933 A | 9/1996 | Numata et al. |
| 6,131,386 A | 10/2000 | Trumble |
| 6,147,503 A | 11/2000 | Nelson et al. |
| 6,507,308 B1 | 1/2003 | Ono et al. |
| 6,630,833 B2 | 10/2003 | Scott |
| 6,819,849 B1 | 11/2004 | Tangonan et al. |
| 6,854,261 B2 | 2/2005 | Williamson et al. |
| 7,157,919 B1 | 1/2007 | Walton |
| 7,357,822 B2 | 4/2008 | Hamahata et al. |
| 7,679,374 B2 | 3/2010 | Bromberg et al. |
| 8,384,396 B2 | 2/2013 | Bromberg et al. |
| 8,384,397 B2 | 2/2013 | Bromberg et al. |
| 8,889,221 B2 | 11/2014 | Sappok |
| 9,144,831 B2 | 9/2015 | Sappok et al. |
| 9,399,185 B2 | 7/2016 | Bromberg et al. |
| 9,400,297 B2 | 7/2016 | Bromberg et al. |
| 2001/0003898 A1 | 6/2001 | Miller et al. |
| 2001/0007571 A1 | 7/2001 | Murphy et al. |
| 2002/0005725 A1 | 1/2002 | Scott |
| 2004/0200198 A1 | 10/2004 | Inoue et al. |
| 2005/0011278 A1 | 1/2005 | Brown et al. |
| 2005/0213548 A1 | 9/2005 | Benson et al. |
| 2005/0241295 A1 | 11/2005 | Breuer et al. |
| 2006/0027511 A1 | 2/2006 | Brown et al. |
| 2006/0070373 A1 | 4/2006 | Huang et al. |
| 2006/0101793 A1 | 5/2006 | Gregoire et al. |
| 2006/0138082 A1 | 6/2006 | Strang |
| 2006/0229466 A1 | 10/2006 | Arhancet et al. |
| 2007/0000218 A1 | 1/2007 | Wirth et al. |
| 2007/0022746 A1 | 2/2007 | Decou et al. |
| 2007/0024289 A1 | 2/2007 | Knitt et al. |
| 2007/0056274 A1 | 3/2007 | Wills |
| 2007/0068157 A1 | 3/2007 | Kurtz |
| 2007/0072567 A1 | 5/2007 | Nagai et al. |
| 2007/0101705 A1 | 5/2007 | Knitt |
| 2007/0125075 A1 | 6/2007 | Zanini-Fisher et al. |
| 2007/0125349 A1 | 6/2007 | Zanini-Fisher et al. |
| 2007/0130923 A1 | 6/2007 | Dye et al. |
| 2007/0169469 A1 | 7/2007 | Knitt |
| 2007/0209333 A1 | 9/2007 | Kondou |
| 2007/0214862 A1 | 9/2007 | Kubinski et al. |
| 2008/0018442 A1 | 1/2008 | Knitt |
| 2008/0059093 A1 | 3/2008 | Bromberg et al. |
| 2008/0066621 A1 | 3/2008 | Naito et al. |
| 2008/0092499 A1 | 4/2008 | Otsuka et al. |
| 2008/0110143 A1 | 5/2008 | Chen et al. |
| 2008/0264036 A1 | 10/2008 | Bellovary |
| 2009/0038294 A1 | 2/2009 | Anderson et al. |
| 2009/0295509 A1 | 12/2009 | Master et al. |
| 2010/0075317 A1 * | 3/2010 | Schneider ............... B03C 3/383 435/6.12 |
| 2010/0101409 A1 | 4/2010 | Bromberg et al. |
| 2010/0102828 A1 * | 4/2010 | Bromberg .......... B01D 46/0086 324/639 |
| 2012/0138093 A1 * | 6/2012 | Sappok .................. B01D 65/02 134/18 |
| 2013/0125745 A1 | 5/2013 | Bromberg et al. |
| 2013/0127478 A1 | 5/2013 | Bromberg et al. |
| 2013/0239666 A1 * | 9/2013 | Carpenter ............ B01D 61/147 73/61.72 |
| 2013/0298530 A1 | 11/2013 | Carlill et al. |
| 2014/0116028 A1 | 5/2014 | Sappok et al. |
| 2015/0123688 A1 | 5/2015 | Sappok et al. |
| 2015/0132187 A1 | 5/2015 | Takaoka et al. |
| 2015/0355110 A1 | 12/2015 | Sappok et al. |
| 2015/0358091 A1 | 12/2015 | Sappok et al. |
| 2016/0018289 A1 * | 1/2016 | Forster .................... F01N 11/00 73/114.75 |

FOREIGN PATENT DOCUMENTS

| | | |
|---|---|---|
| DE | 3317215 A1 | 11/1983 |
| DE | 102004016725 A1 | 2/2006 |
| EP | 0097416 A1 | 1/1984 |
| EP | 0356040 A2 | 2/1990 |
| JP | 4-505665 A | 10/1992 |
| WO | 92/02807 A1 | 2/1992 |
| WO | 93/05388 A1 | 3/1993 |
| WO | 00/50743 A1 | 8/2000 |
| WO | 2004/074670 A2 | 9/2004 |
| WO | 2005/060653 A2 | 7/2005 |
| WO | 2005/093233 A1 | 10/2005 |
| WO | 2006/002037 A1 | 1/2006 |
| WO | 2007/130896 A2 | 11/2007 |
| WO | 2009031600 A2 | 3/2009 |
| WO | 2010/074812 A1 | 7/2010 |
| WO | 2011/156477 A2 | 12/2011 |
| WO | 2014064406 A1 | 5/2014 |
| WO | 2015/188188 A1 | 12/2015 |
| WO | 2015/188189 A1 | 12/2015 |

\* cited by examiner

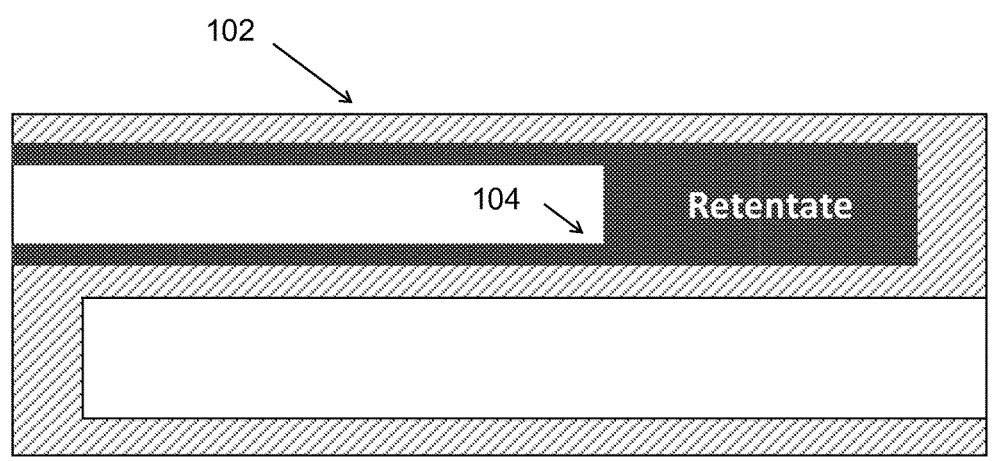

FILTER RETENTATE ANALYSIS AND DIAGNOSTICS

This application claims priority of U.S. Provisional Patent Application Ser. No. 62/065,761, filed Oct. 20, 2014, the disclosure of which is hereby incorporated by reference in its entirety.

BACKGROUND OF THE INVENTION

Removal and analysis of materials collected in filters provides important information useful to ascertain or diagnose the history or operating state of the system with which the filters are used.

Examples to illustrate the broad applicability of filter retentate analysis include filters used in commercial and industrial processes and applications. Analysis of the material collected on the filters and comparison with known standards or reference materials provides information on the state of the system generating the retentate. In this manner, information may be obtained to discern the operating history or changes in operation of the system generating the retentate during the period in which the filter is in service.

One particular example includes particulate filters, such as diesel particulate filters or gasoline particulate filters, but any filter or retentate collection media or system may be used. In the case of a particulate filter installed in the exhaust of an engine or other system (plant or process) generating retentate, the filter captures and collects retentate produced by the system. While effective at capturing retentate, the use of filters also has some disadvantages.

First, the filter may mask or hide signs of engine, plant, or process malfunctions or failures. For example, leaks of fluids, gases, or the generation of other emissions or effluent from the engine, plant, or process which otherwise may be directly visible to the operator may also be collected on the filter. In the case of an exhaust particulate filter, signs of engine malfunctions such as blue, black, or white smoke exiting the tailpipe may no longer be visible, as the smoke or vapors are captured on the filter.

Second, the accumulation of retentate generated as a result of a system malfunction, such as particles, liquids, or other components for which the filter was not intended, may also cause damage to the filter. In one example, an engine oil leak, coolant leak, or improper combustion may lead to the accumulation of coolant, oil, fuel, or high levels of soot on the exhaust particulate filter, which could adversely affect filter performance and service life, in addition to that of the engine, process, or plant.

In many cases, filters are periodically removed for cleaning or reconditioning so that they can be reused, rather then replaced. In many cases, the filter cleaning or reconditioning involves removal of the retentate from the filter. Common methods of filter cleaning involve the use of forced air to blow the retentate out of the filter, liquid-based cleaning or washing methods, thermal cleaning, the use of vibrations, and other related means. Most filter cleaning systems and processes further aggregate and collect the retentate removed form the filters in a bulk collection system, such as a liquid storage tank, dust collection system, and the like. The use of these conventional bulk cleaning processes has several drawbacks as well.

First, collection of the bulk retentate removed or cleaned from the filters in aggregate collection systems, such as a dust collection system or liquid storage tank, does not allow for the retentate to be uniquely identified or linked to the filter from which it was removed. Thus, any subsequent analysis of the retentate will not enable any useful diagnosis of the filter state or engine/equipment that generated the retentate, as all of the retentate is mixed together in the bulk collection system from various sources.

Second, cleaning methods which destroy, alter, or in any other way affect or modify the properties of the retentate, such as its characteristics, or physical or chemical properties, further preclude any meaningful analysis and diagnosis of the stat of the engine, equipment, plant, process, or filter from which the retentate originated.

Therefore, a retentate removal or collection system is desired, which would allow the retentate removed from a particular filter to be uniquely linked or identified by the filter from which it was removed. Note in some cases it may not be necessary to remove the retentate from the filter but rather to remove a small portion of the filter containing the retentate for analysis, or conduct the analysis of the retentate on the filter directly, without removing the retentate or altering the filter. In addition, it is highly desirable to avoid or minimize any changes to the retentate prior to the analysis.

Therefore, an improved process of collecting and analyzing retentate is needed, which will have considerable utility for a broad range of applications and fields of uses.

SUMMARY OF THE INVENTION

A filter retentate analysis system and method is disclosed, which provides information to diagnose the current and historical state of a system generating the retentate or through which the retentate has passed. The disclosure describes the analysis of retentate characteristics which may include the composition, amount, distribution, and physical or chemical properties of the retentate useful to monitor or diagnose the state, health, or operating history of a system or sub-system. The analysis is broadly applicable to wide range of systems and process ranging from engines and exhaust systems to production plants and equipment.

BRIEF DESCRIPTION OF THE FIGURES

FIG. 1 represents a channel in a particulate filter containing retentate. FIG. 1 is a cross-sectional view of two channels of a cellular ceramic particulate filter containing retentate according to one embodiment.

DETAILED DESCRIPTION OF THE INVENTION

This invention relates to a system for removing and analyzing material collected in filters (retentate) as well as methods of material removal, analysis, and interpretation of the results. The retentate analysis system and method described in this disclosure, enables direct collection of the retentate from individual filters, and analysis of the retentate to provide information useful to diagnose the present state or past history of the engine, plant, process, or system generating the retentate.

FIG. 1 depicts a cut-away view of a two-channels 102 channel in a particulate filter containing retentate 104.

The retentate 104 may be analyzed, either in the filter, or after being removed from the filter to obtain information useful to diagnose the operating conditions or history of the filter 102 or any systems or equipment connected to or in communication with filter 102.

Analysis of the retentate material removed from the filter or contained in the filter 102 may include one or more of the following parameters:

1. Amount of Retentate: such as the amount of a solid, liquid, or gas-phase component collected in or on the filter media or retentate collection system. In one example, the amount of soot or ash constituent collected on a filter or the amount of a liquid phase component absorbed by the filter or even a gas phase component adsorbed on a filter or catalyst or adsorbed/absorbed into the solid retentate may be quantified. In one example, the amount of material collected on the filter above or below some threshold value may be a sign of a fault or error condition.
2. Type of Material: such as the composition of one or more than one type of material or species.
3. Spatial Distribution: such as the location of the retentate or component of the retentate on the filter.
4. Physical or Chemical Properties of the Retentate: such as its chemical composition (identification of certain compounds or elements), or the chemical state, such as the oxidation or reduction state, polarity, pH, or other chemical property, crystal structure, phase, particle size, porosity, density, color, or any other relevant physical or chemical property.

The above list illustrates several major categories of parameters which may be monitored or analyzed, but is by no means exhaustive. Many other parameters may also be monitored or analyzed.

The general steps involved in conducting the analysis and interpreting or drawing conclusions from the analysis are described below:

1. A first optional step is the removal of one or more retentate samples from the filter, the retentate being removed from one or more filter locations.
2. A second step consists of the analysis of the retentate either removed from the filter or still contained on the filter directly.
3. A subsequent step involves comparison of the retentate analysis results with a reference and the formulation of one or more conclusions or diagnoses based on the comparison.

The steps listed above may not all be required, and those skilled in the art will certainly realize the steps may be carried out in another sequence without deviating from the intent and scope of the invention.

In certain embodiments, the steps added are followed by the performance of a corrective action.

The invention will now be described with reference to a particular application and embodiment, which is a particulate filter installed in the exhaust of an internal combustion engine, which may be a diesel engine, gasoline engine, natural gas engine, or any other engine such as a turbine engine or reciprocating piston engine or the like.

In the case of the particulate filter, the filter accumulates retentate which may be the result of inputs to the engine such as fuel, lubricant, coolant, or material in the intake air stream, as well as retentate originating from the engine components themselves, such as wear debris, and retentate originating from the exhaust system, such as the exhaust conduit and any components in the exhaust system upstream of the filter, such as other catalysts or filters.

The retentate collected in the filter may be generally categorized as soot and ash but may be any material including solids, liquids, or gases. In one embodiment, the filter may be removed from the exhaust system and subject to a process to remove some or all of the retentate. The process may involve removal through the application of one or more vibrations or impacts to dislodge and remove the retentate, the application of forced air or some other gas to blow the retentate off the filter, or liquid cleaning or washing means, heating or regeneration, or any other means to remove the retentate. In another embodiment, the retentate may be removed from a particular region of the filter, such as by physical extraction, scraping, swabbing, wiping, the application of vacuum or suction, or any other means to obtain a sample of the retentate from the filter. Regardless of the removal means, the removed retentate must be collected to uniquely identify the filter from which it originated.

Under some circumstances, the retentate is removed such that its axial location in the trap or filter is recorded and segregated, especially when the retentate time of accumulation is related to its location in the filter. This approach will provide useful information on the history of the plant or engine, when the retentate is transported and accumulated or builds up in the rear of the filter, in one example.

Retentate collection means include the use of sample bags, filters, vials, jars, swabs, applicators, tubular extraction or sampling devices, or any other means to collect the retentate.

In another embodiment, the retentate need not be removed from the filter, but may be analyzed directly on the filter media.

The retentate analysis, in the case of a particulate filter, may include analysis of the amount, composition, characteristics, and properties of the retentate useful to diagnose the state or condition of the engine, vehicle, filter or equipment. In one example, elemental or compositional analysis of the retentate may be conducted using inductively coupled plasma (ICP), energy dispersive x-ray analysis (EDX), x-ray fluorescence (XRF), Fourier transform infrared (FTIR) analysis, Raman spectroscopy, mass spectroscopy, spark-optical emission spectroscopy (OES) or LIBS (Laser induced breakdown spectroscopy), neutron activation analysis (NAA) or any other technique which provides information on the elements or chemical compounds present in the retentate. Results of the analysis may be compared with references of the known sources of the materials or constituents found in the retentate. In another embodiment, no references may be used. The interpretation of the results may be from experience or existing know-how, or comparison with known materials, standards, or reference data in another example.

The comparison of retentate to references or other data may be performed by a controller, such as a processing unit in combination with a storage element. The processing unit may receive the analysis from any of the system described above, and perform the comparison. In certain embodiments, the reference values are stored in the storage element.

In the case of a particulate filter, the references may include knowledge of the chemical compounds or elements present in the fuel, lubricant oil, or coolant, as well as compounds or elements present in the operating environment of the engine or equipment, in addition to elements and compounds present in the engine or exhaust system itself.

In one example, the engine lubricant may contain additives, such as calcium, zinc, boron, magnesium, sulfur, phosphorus, molybdenum, and any other type of additive elements. Detection of these materials in the filter may be related back to the engine oil consumption to diagnose abnormal oil consumption, such as high levels of these elements in the filter, or even a liquid oil leak, such as from the turbocharger or valve seals, in another example.

Further, metallic elements including iron, aluminum, tin, lead, chromium, titanium, copper, and others which are often found in engine components, such as bearings, pistons, cylinder walls, liners, valves, and other components may also be found in the filter. Detection of these materials or related materials in the filter may be used to diagnose early signs of component failure such as bearing wear, in one example, or excessive rust or corrosion in another example.

Catalyst elements such as precious metals, including platinum, palladium, rhodium, vanadium, copper, iron, and others as well as washcoat components including ceria, alumina and even substrate components may also be detected in the retentate collected in the filter. Detection of these elements may be used to diagnose the state or detect signs of failure of catalysts or other emission control components upstream of the filter.

Fuel-derived elements including sulfur, or sodium or potassium, as in the case of alternative fuels or biofuels, or fuel additive components including platinum and iron, may also be detected in the filter and used to diagnose the quality and/or composition of the fuel or fuel additives used with the engine. Similarly, coolant-derived elements, including silicon, may also be detected in the filter to diagnose signs of a coolant leak.

Environmental sources, such as ambient dust, dirt, salt spray (sodium chloride), minerals, and other material resulting from the environment in which the engine or equipment is operating may also be detected in the filter and used to diagnose the state of the intake air filtration system of the engine or equipment.

The analysis need not be limited solely to chemical or compositional analysis, but also to visual analysis or inspection of the retentate as well as characterization of the retentate properties, whether in solid, liquid, or gaseous form. For example, liquid oil, fuel, or coolant, or wet spots on the filter may be readily observed and provide an indication of an engine or equipment malfunction. High levels of soot or ash may also be used to indicate abnormal engine operation or combustion, of failure or signs of failure of the engine or related sub-systems. In another example, the chemical or physical properties, composition, or structure of the retentate, such as crystal structure, may be an indication of previous temperature history of the retentate or filter.

Analysis may include separation of retentate components or removal of certain components such as via oxidation, or inducing preferential changes in the components, such as through intentional chemical reactions. In one example, the reactions may be through the application of acids, microwaves, heating, or the like. In one example, the reactions may include sample preparation or digestion for ICP. In another example, the analysis may include decomposition of the retentate such as by heating or chemical reaction and analysis of the reaction products or effluent to determine the retentate composition or properties, such as sulfur content in one example. In another example, thermal analysis techniques, such as thermo-gravimetric analysis or TGA may be used.

In another example, the analysis may include a historical trend analysis to track and evaluate the quantity and/or properties and characteristics, such as composition, of the retentate in the filter over time. In another embodiment, the analysis may include comparison of individual data points or collections of historical data points with a reference in one example, or with average values from a larger population of samples in another example. Statistical analysis or trend analysis may or may not be applied, and comparison with a reference may or may not be required.

In another example, the source of unknown retentate constituents may be determined by:
1. Collecting samples from the inputs to the engine, process, plant, or system, such as the fuel, oil, coolant, and any other system inputs.
2. Collecting samples from the ambient environment in which the engine or equipment is operating.
3. Collecting samples or determining the composition of the various components and systems comprising the engine, plant, process, equipment or system.
4. Collecting samples from any additional components that may be in communication with the filter.
5. Analyzing the characteristics such as composition and chemical or physical properties of the samples items from steps 1-4.
6. Comparing the results of the filter retentate analysis with the sample analysis in step 5 and determining by means of comparison the source of the unknown retentate constituents.
7. Determining whether the unknown retentate constituent identified in step 6 is acceptable or not (whether additional corrective action is warranted).

In this manner, the source of the constituents comprising the retentate may be identified, in order to determine whether the engine, equipment, filter, process, plant or system is operating in an acceptable manner or whether the unknown retentate constituents are an indication of an underlying problem which may need to be addressed.

In each of these embodiments, the diagnosis may be followed by a corrective action. This corrective action may include: repair or replacement of an oil filter, gasket or seal; repair or replacement of a bearing, piston, valve or other component; repair or replacement of a catalyst or other emission control component; repair of a coolant leak; replacement or repair of the intake air filtration system.

Care should be taken when removing or collecting filter retentate or any samples useful for draw comparisons with the filter retentate to avoid contaminating, disturbing, or in any other manner unintentionally altering the retentate or sample. Such care may require the use of careful sampling and handling procedures, as well as tools or equipment.

The retentate sampling and analysis system may include a filter containing retentate, a retentate removal and collection system, and a retentate analysis system, such as an instrument to analyze the physical or chemical properties of the retentate. In one example, the filter may be a cellular ceramic particulate filter, and the retentate removal system may be a vibration cleaning system, and the retentate collection system may be a catch pan or ash bin, and the analysis instrument may be an ICP analyzer. In another example, an extraction tool, such as a suction tube or hollow tube, may be used to collect and remove the retentate from the filter. In another example, the retentate removal system may be a pneumatic cleaning system. In yet another example, the retentate need not be removed from the filter.

In-situ analysis of the retentate can be performed without the need to remove the retentate from the filter. For example, LIBS analysis through the use of a laser system through the open channel (without illumination of the filter walls) can provide in-situ information on the elemental composition of the retentate, with observation through the same open channel. Similarly, spark-OES can be used, with the discharge (spark) generated inside the channel by appropriate electrodes. Non-optical techniques can also be used, such as NAA and CT-scan. In another example XRF may be used.

Those skilled in the art will surely realize that the steps described above may be carried out in another sequence without deviating from the intent and scope of the invention.

While particular embodiments of the invention have been shown and described, it will be obvious to those skilled in the art that various changes and modifications may be made without departing from the present invention in its broader aspects. It is intended that all matter contained in the above description and shown in the accompanying drawings shall be interpreted as illustrative and not in a limiting sense.

What is claimed is:

1. A method of diagnosing an engine system generating retentate in communication with an engine exhaust system particulate filter in an engine exhaust system and containing the retentate generated by the engine system, comprising:
    removing the retentate contained in the engine exhaust system particulate filter;
    analyzing the physical or chemical properties of the retentate removed from the engine exhaust system particulate filter including detecting the presence in the retentate of the physical or chemical properties of a compound or element of the engine system or the engine exhaust system; and
    diagnosing the engine system based on the analysis and detection of the physical or chemical properties of the engine compound or element in the retentate.

2. The method of claim 1, where the analyzing the physical or chemical properties of the retentate removed from the engine exhaust system particulate filter in the engine exhaust system is performed using inductively coupled plasma (ICP), energy dispersive x-ray analysis (EDX), x-ray fluorescence (XRF), Fourier transform infrared (FTIR) analysis, Raman spectroscopy, mass spectroscopy, spark-optical emission spectroscopy (OES), LIBS (Laser induced breakdown spectroscopy), neutron activation analysis (NAA) or any other technique which provides information on the elements or chemical compounds present in the retentate.

3. The method of claim 1, further comprising the step of collecting the retentate removed from the engine exhaust system particulate filter including the use of collecting means selected from the group consisting of sample bags, filters, vials, jars, swabs, applicators, tubular extraction, catch pan, ash bin or sampling devices.

4. The method of claim 1, wherein the removal of the retentate from the engine exhaust system particulate filter includes the use of removal means selected from the group consisting of vibration cleaning system, an extraction tool, and a pneumatic cleaning system.

5. The method of claim 1 wherein the step of analyzing the physical or chemical properties of the retentate removed from the engine exhaust system particulate filter includes the analysis of the amount, composition, characteristics, and properties of the retentate useful to diagnose the state or condition of the engine system.

6. The method of claim 1 further comprising the step of comparing the physical or chemical properties of the retentate removed from the engine exhaust system particulate filter with references of the known sources of materials or constituents found in the retentate.

7. The method of claim 6 wherein the references include knowledge of the physical or chemical properties of the chemical compounds or elements present in the fuel, lubricant oil, or coolant of the engine system including compounds or elements present in the operating environment of the engine system or engine exhaust system.

8. The method of claim 1 wherein the analyzing step includes the step of separating or removing certain of the components of the retentate removed from the engine exhaust system particulate filter.

9. The method of claim 1 wherein the analyzing step includes a historical trend analysis for tracking and evaluating the quantity and/or physical or chemical properties of the retentate removed from the engine exhaust system particulate filter over time.

* * * * *